US012458701B2

(12) United States Patent
Desai et al.

(10) Patent No.: US 12,458,701 B2
(45) Date of Patent: Nov. 4, 2025

(54) BIS (HYDROXY BENZYLIDENE) CYCLIC KETONE BASED TETRA-AZA CORAND

(71) Applicants: Arpita Desai, Gujarat (IN); Priyanka Mathur, Gujarat (IN)

(72) Inventors: Arpita Desai, Gujarat (IN); Priyanka Mathur, Gujarat (IN)

( * ) Notice: Subject to any disclaimer, the term of this patent is extended or adjusted under 35 U.S.C. 154(b) by 245 days.

(21) Appl. No.: 17/639,918

(22) PCT Filed: Oct. 6, 2021

(86) PCT No.: PCT/IN2021/050960
§ 371 (c)(1),
(2) Date: Mar. 3, 2022

(87) PCT Pub. No.: WO2022/074673
PCT Pub. Date: Apr. 14, 2022

(65) Prior Publication Data

US 2023/0226194 A1 Jul. 20, 2023

(30) Foreign Application Priority Data

Oct. 6, 2020 (IN) ............................. 202021043486

(51) Int. Cl.

| | |
|---|---|
| ***C07D 487/22*** | (2006.01) |
| ***A61K 47/54*** | (2017.01) |
| ***C07D 257/10*** | (2006.01) |
| ***C07D 487/18*** | (2006.01) |

(52) U.S. Cl.
CPC .......... *A61K 47/545* (2017.08); *C07D 257/10* (2013.01); *C07D 487/18* (2013.01); *C07D 487/22* (2013.01)

(58) Field of Classification Search
None
See application file for complete search history.

(56) References Cited

PUBLICATIONS

Borisova et al., “Metal-Free Methods in the Synthesis of Macrocyclic Schiff Bases” Chem Rev vol. 107 No. 1 pp. 46-79, DOI: 10.1021/cr0683616 (Year: 2007).*
Perez et al., “Synthesis of Multidentate 1,3,4-Oxadiazole-, Imine-, and Phenol-Containing Macrocycles” J Org Chem vol. 58 pp. 2628-2630 (Year: 1993).*
Roy et al., “Synthesis of Calix-Salen Silver Corates for Evaluation of Their Antimicrobial and Anticancer Activities” ACS Omega vol. 4 pp. 21346-21352, DOI: 10.1021/acsomega.9b02948 (Year: 2019).*

* cited by examiner

*Primary Examiner* — Eric Olson
(74) *Attorney, Agent, or Firm* — Rivka Friedman

(57) ABSTRACT

A tetra-aza corand compound of formula (Ia) and compound of formula (Ib) and salts thereof. The tetra-aza corand of formula (Ia) and (Ib) of the present invention relates to novel corand entity having a substantially enclosed volume and a framework structure, the compounds are designed as therapeutic carriers for molecule therapeutics delivery and pharmaceutical compositions thereof.

5 Claims, 9 Drawing Sheets

BIS (HYDROXY BENZYLIDENE) CYCLIC KETONE BASED TETRA-AZA CORAND

FIELD OF THE INVENTION

The present invention relates to novel bis(hydroxybenzylidene)cyclicketone based tetra-azacorand of formula (Ia) and (Ib) and salts thereof. The corand of formula (Ia) and (Ib) comprises cycloalkane-1,2-diamine units covalently bonded to 2,6-bis((E)-4, hydroxybenzylidene)cyclic ketone compounds of Formula (I) via imino or methyl amino linkages. The present invention relates to Bis(hydroxybenzylidene) cyclic ketone based tetra-aza corand of formula (Ia) and (Ib) having a substantially enclosed volume and a framework structure are designed as therapeutic carriers for molecule therapeutics delivery and pharmaceutical compositions thereof.

peutic agent. Often when delivering drugs to an individual, there is a need to reduce the diffusion rate of the drugs into tissue and capillaries where the drug is not required, as the drug ideally enters the arterial system for delivery around the body. Also delivery should be such that it is possible to extend the effect of the drug locally over a period of time and this is often done by way of an injectable solution containing liposome encapsulated drugs.

The design and synthesis of water-soluble, tailor-maid synthetic macrocycles as an effective tool for development of drug delivery system has been a key subject of interest in recent years. Self-assembly of such synthetic receptors with biorelevant molecules is a potent tool for the understanding, mimicking and modelling of biological systems and evolving new materials with precise properties and roles. The most exploited macrocycle for drug delivery studies are cyclodextrin and its analogues. Along with the cyclodex- Formula (Ia)

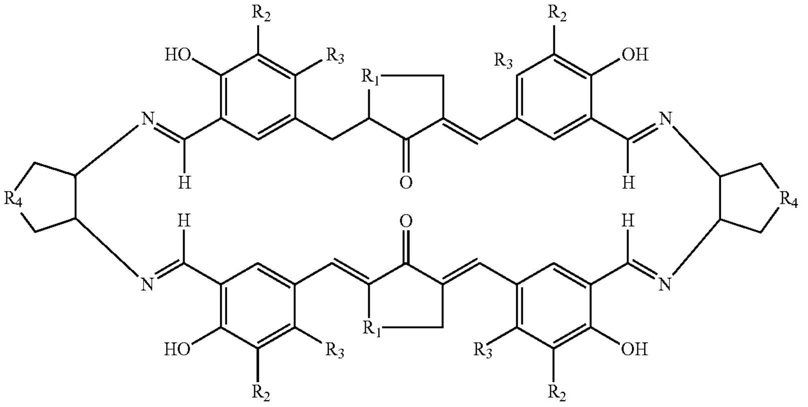

OR

Formula (Ib)

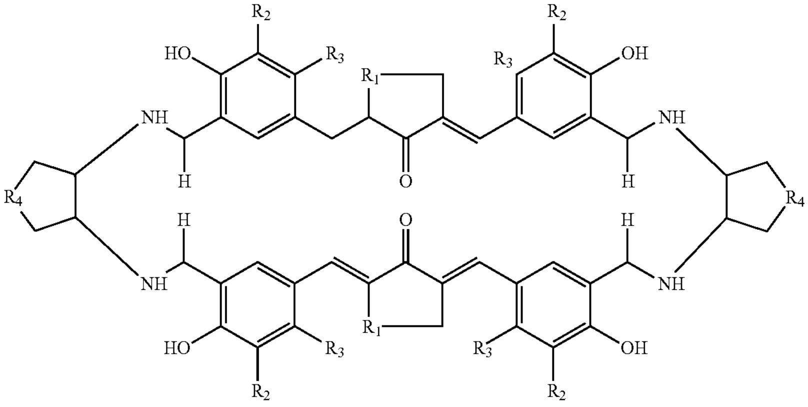

BACKGROUND OF THE INVENTION

The encapsulation of pharmaceuticals is known but these methods involve the encapsulation of materials that are then stored before being used. The preparations typically are stored and then transported to locations where the drug is prescribed and administered. This means that there may be a relatively long period between manufacture of the compositions and delivery to a patient. This occurs in a wide range of areas where materials are administered to an individual, including the treatment of humans, veterinary applications and during drug delivery with specialised medical devices which are used to control the administration of drugs, for example in the administration of a chemotheratrins, crown ethers, cryptands and calix[n]arenes are other important categories of supramolecular macrocylic hosts capable of encapsulating the drug molecule in their cavities. Corands are defined as monocyclic polydentate macrocyclic compounds, usually uncharged, in which three or more coordinating ring atoms (usually oxygen or nitrogen) are present. Crown ethers are part of corand family. Crown ether amphiphiles have been synthesized for development of a sustained drug release system. The capability of these vesicles as efficient drug delivery systems has been evaluated by encapsulating an antineoplastic drug, 5-fluorouracil. (Muzzalupo, R., Nicoletta, F. P., Trombino, S., Cassano, R., lemma, F., Picci, N., Colloids and Surfaces B: Biointerfaces, 2007, 58, 197-202) Furthermore, azacorand compounds containing nitrogen donor atoms are also reported in the literature. A series of bifunctional derivatives of pyridine-azacrown compounds are reported in the literature. The derivatives are expected to undergo coupling reactions with a wide range of biological vectors to create bioconjugates capable of targeted drug delivery to malignant cells without destroying healthy tissue. (Zubenko, A. D., Shchukinaa, A. A., Fedorovaa, O. A. Synthesis, 2019, 51, A-I.).

Calix[n]arenes are third generation macrocylic hosts with a high degree of steric flexibility which confers on them many applications. There exist four conformational isomers of calixarenes, and a large number of cavities of various sizes and shapes, which can be employed for molecular recognition processes. Along with calix[n]arene, the resorcinarenes and pyrogallolarenes have been the focus of current research because of the presence of both hydrophobic and hydrophilic sites in the basket-shaped cavity. The polarity, size, and other properties of the cavity can be further altered by functionalization, which helps the macrocycles to encapsulate ions and neutral molecules. (Harrowfield, J. Chem. Commun., 2013, 49, 1578.), (Vinodh, M., Alipour, F. H., Mohamod A. A., AlAzemi, T. F. Molecules, 2012, 17, 11763-11799.), (Song, J., Li, H., Chao, J., Dong, C., Shuang, S. J. Inclusion Phenom. Macrocyclic Chem., 2012, 72, 389-395.). The inclusion complexes of drug molecule generally show improved physical characteristics, such as enhanced solubility in water and reduced toxicity in biological systems etc. The calixarene encapsulated drug complex can respond to external stimuli, rendering the prolonged and control release of the drug which suggests its potential application as a drug delivery system.

The most significant limitation of calix[n]arenes has been their low aqueous solubility. However functionalization with polar groups or moieties such as sulfonates (Kunsagi-Mate, S., Szabo, K., Lemli, B., Bitter, I., Nagy, G., Kollar, L. Thermochim. Acta, 2005 425, 121-126.) (Perret, F., Lazar, A. N., Coleman, A. W. Chem. Commun. (Camb), 2006, 2425-2438.), amines, aminoacids, peptides and saccharides (Casnati, A., Sansone, F., Ungaro, R., Acc. Chem. Res. 2003, 36, 246-254. Fulton, D. A., Stoddart, J. F., Bioconjug. Chem. 2001, 12, 655-672.) (Krenek, K., Kuldova, M., Hulikova, K., Stibor, I., Lhotak, P., Dudic, M., Budka, J., Pelantova, H., Bezouska, K., Fiserova, A., Kren, V., Carbohydr. Res. 2007, 342, 1781-1792.), (Shahgaldian, P., Sciotti, M. A., Pieles, U., Langmuir 2008, 24, 8522-8526.), phosphonates (Martin, A. D., Raston, C. L., Chem. Commun. (Camb) 2011, 47, 9764-9772.), poly(ethylene oxide) (PEO) (Gao, Y., Li, Z., Sun, M., Li, H., Guo, C., Cui, J., Li, A., Cao, F., Xi, Y., Lou, H., Zhai, G., Drug Dev. Ind. Pharm. 2010, 36, 1225-1234.), (Taton, D., Saule, M., Logan, J., Duran, R., Hou, S., Chaikof, E. L., Gnanou, Y., J. Polym. Sci. Part A: Polym. Chem. 2003, 41, 1669-1676) has been reported to increase the aqueous solubility of calix[n]arenes. Testosterone was successfully encapsulated within p-sulfonated calix[n]arene. (Millership, J. S, J. Incl. Phenom. Macrocycl. Chem. 2001, 39, 327-331). p-Sulfonato-calix[n]arenes in acidic aqueous solution are studied with three practically insoluble drugs, niclosamide, nifedipine, and furosemide for solubilisation. (Yang, W., De Villiers, M. M, AAPS J. 2005, 7, 241-248.), (Yang, W., De Villiers, M. M. Eur. J. Pharm. Biopharm. 2004, 58, 629-636.) (Yang, W., De Villiers, M. M, J. Pharm. Pharmacol. 2004, 56, 703-708.) (Yang, W., Otto, D. P., Liebenberg, W., De Villiers, M. M, Curr. Drug Discov. Technol., 2008, 5, 129-139) p-sulfonated calix[4]arene is also reported for delivery of antibacterial drug norfloxacin. (Lu, Q., Zhou, Y., Sun, J., Wu, L., Yu, H., Xu, H., Wang, L., Comb. Chem. High Throughput Screen. 2007, 10, 480-485).

The ability to direct a drug payload specifically and exclusively to a particular cellular site is regarded as a Holy Grail in chemotherapy. Most of the anticancer drugs equally affect tumor as well as healthy cells which leads to the significant toxicity. To deal with the toxicity of the anticancer drugs towards healthy human cells, several targeting drug delivery approaches have been emerged with various degrees of success. One approach is to design pH-sensitive polymeric composite to trigger the release of a drug cargo upon extravasations into cancer tissues, the ideal system being capable of responding with adequate discrimination to the small pH difference between blood (pH 7.4) and tumour milieu (pH 5.5) (Torchilin, V. P. Nat. Rev. Drug Discov. 2005, 4, 145-160), (Jiang, L., He, B., Pan, D., Luo, K., Yi, Q., Gu, Z. J. Biomed. Nanotechnol. 2016, 12, 79-90), (Jiang, L. et al. Jiang, L., Li, L., He, X., Yi, Q., He, B., Cao, J., Pan, W., Gu, Z. Biomaterials 2015, 52, 126-139.) Another approach is to target receptors that are overly expressed on cancer cell membranes, like the folate receptor (FR) which has been the target of choice for a various range of delivery platforms, such as pegylated micelles, (Y., Jang, W. D., Nishiyama, N., Fukushima, S. & Kataoka, K, MolBiosyst 1, 2005, 242-250), (Wang, Y. et al. Int J Pharm, 2012, 434, 1-8. Gao, X. et al. J Biomed Nanotechnol, 2015, 11, 578-589) derivatised liposomes (Zhao, X. B., Lee, R. J. Adv Drug Deliver Rev, 2004, 56, 1193-1204) and vesicles modified with acid-triggered drug releasing mechanisms (Rui, Y., Wang, S., Low, P. S., Thompson, D. H. J Am Chem Soc, 1998, 120, 11213-11218). Folic acid is relatively inexpensive and commercially available molecule which can be derivatised without losing its FR binding efficiency (Muller, C. & Schibli, R. J Nucl Med, 2011, 52, 1-4) Folic acid (FA) plays a vital role in cell division and DNA synthesis. Significant up regulation of FR in a number of epithelial cancers, like ovarian tumors (Lu, Y. & Low, P. S. Adv Drug Deliver Rev, 2002, 54, 675-693) is found to meet the increased demand for FA during cell proliferation. Binding of FA to the membrane FR initiates FA internalization as well as any drug delivery platform strategically associated with the FA. Subsequent sequestration of the contents into acidic endosomes confirms that the method not only result in cancer-directed drug delivery, but also has the potential to enhance cellular uptake of the delivered drug.

In the above prior art there are no reports of tetra aza macrocycles being made up of bis-hydroxybenzylidene cyclic ketone moiety.

Drug delivery of some molecule therapeutic agents, such as Flutamide, Nilutamide, Methotrexate, Gemcitabine, Doxorubicin and Cisplatin has been problematic due to their poor pharmacological profiles. These therapeutic agents often have low aqueous solubility, their bioactive forms exist in equilibrium with an inactive form, or high systemic concentrations of the agents lead to toxic side-effects. Some approaches to circumvent the problem of their delivery have been to conjugate the agent directly to a water-soluble polymer such as hydroxypropyl methacrylate (HPMA), polyethylene glycol, and poly-L-glutamic acid, in some cases, such conjugates have been successful in solubilizing or stabilizing the bioactive form of the therapeutic agent, or achieving a sustained release formulation which circumvents complications associated with high systemic concentrations of the agent.

The inventors have succeeded in synthesizing new carrier compounds capable of overcoming the technical defects of the encapsulated therapeutic molecule/compounds by their encapsulation via non-covalent interactions followed by controlled delivery of the therapeutic molecule. Said compounds called "tetra-azacorands" made up of bis-hydroxybenzylidene cyclic ketone moiety have a rigid cavity in which the therapeutic molecule/compounds will be trapped via non-covalent interactions. There is an on-going need for new approaches to the delivery of small therapeutic agents that have poor pharmacological profiles such as Flutamide, Nilutamide, Gemcitabin, Dasatinib, Methotrexate, Cis-platin.

SUMMARY OF THE INVENTION

The present invention relates to a novel bis(hydroxybenzylidene) cyclic ketone based tetra-aza corand of formula (Ia) and formula (Ib).

Formula (Ia)

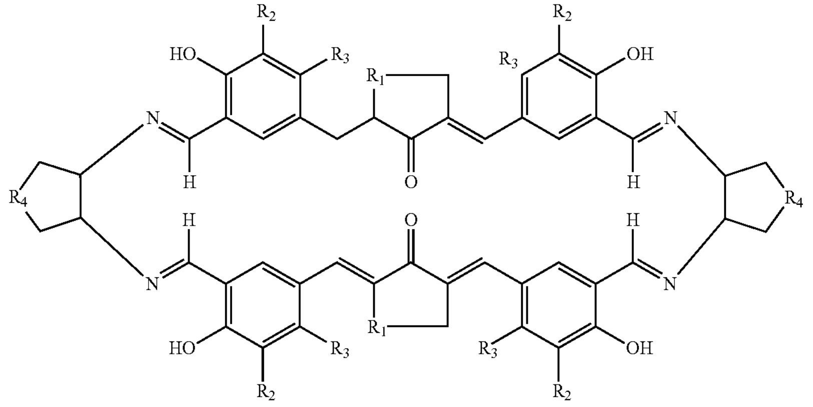

OR

Formula (Ib)

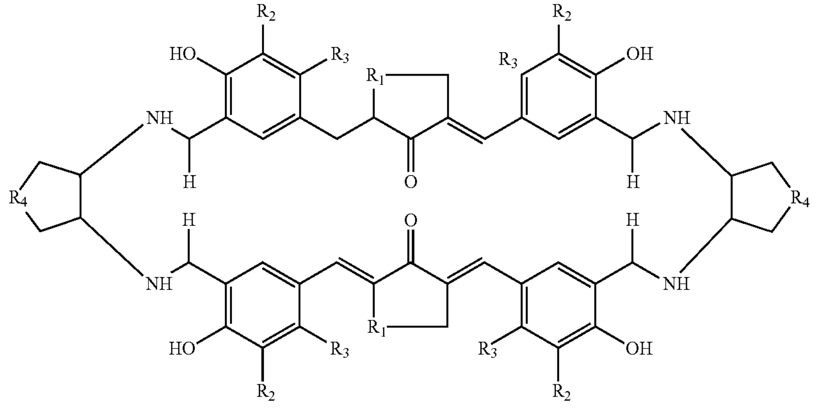

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

According to an another aspect the present invention provides a process of preparation of tetra-aza corand of formula (Ia) comprising reaction of cycloalkane-1,2-diamine with 2,6-bis((E)-4, hydroxybenzylidene)cyclic ketone of formula (I)

Formula (Ia)

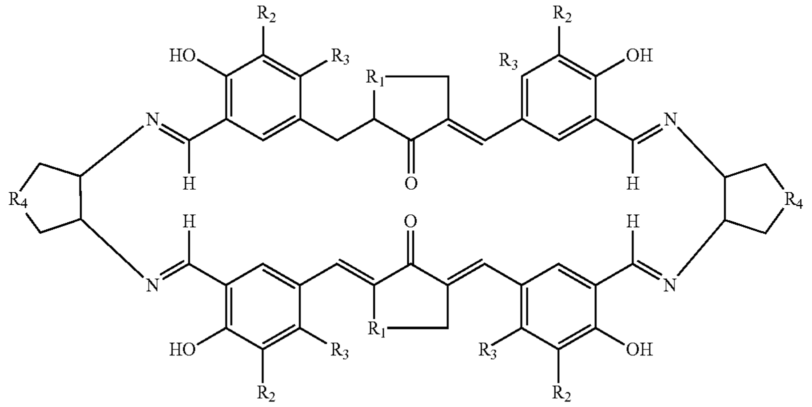

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

According to a another aspect the present invention provides a process of preparation of tetra-aza corand of formula (Ib) comprising reaction of cycloalkane-1,2-diamine units and 2,6-bis((E)-4, hydroxybenzylidene) cyclic ketone of formula (I):

Formula (Ib)

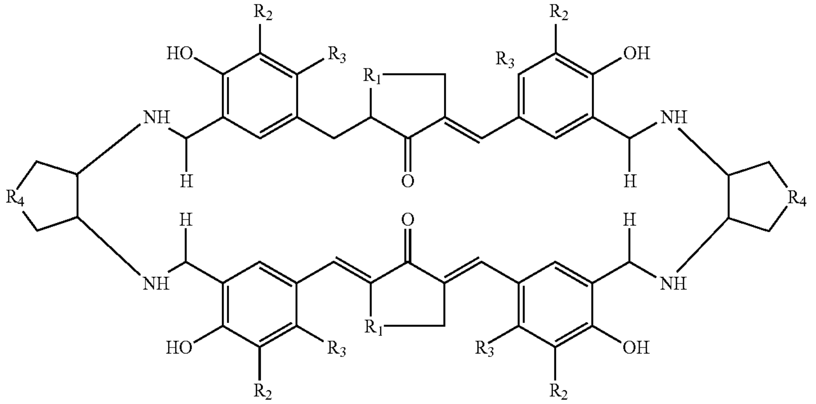

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

In another aspect the present invention provides tetra-aza corand of formula (Ia) and formula (Ib) comprises cycloalkane-1,2-diamine units covalently bonded to 2,6-bis((E)-4, hydroxybenzylidene) cyclic ketone compounds of Formula (I) units configured to form a three-dimensional interior cavity which provides a binding site for large molecules.

Formula (I)

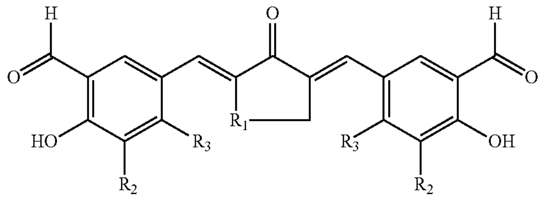

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, In another aspect the present invention provides tetra-aza corands of formula (Ia) and formula (Ib) wherein therapeutic molecule is encapsulated by non-covalent interactions. The tetra-aza corands encapsulate therapeutic molecule/compounds by non-covalent interactions for the controlled delivery of the therapeutic agents. The methods of local delivery of therapeutic molecule/compound encapsulated within tetra-aza corand reduces the toxicity.

In another aspect the present invention provides tetra-aza corand of formula (Ia) and formula (Ib) configured to form a three-dimensional interior cavity which provides a binding site for large molecules, having a substantially enclosed volume and a framework structure, the compounds are designed as therapeutic carriers for therapeutics molecule delivery and pharmaceutical compounds such as Flutamide, Nilutamide, Gemcitabin, Dasatinib, Methotrexate, Cis-platin.

In another aspect the present invention provides tetra-aza corand compound of formula (Ia) has isomeric form as (1R,2R) tetra-aza corand of formula (Ia')

Formula (Ia')

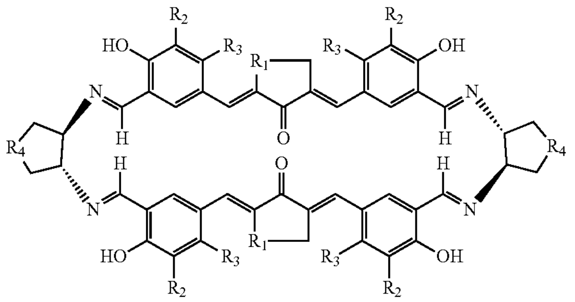

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

In another aspect the present invention provides tetra-aza corand compound of formula (Ib) has isomeric form as (1R,2R) tetra-aza corand of formula (Ib')

Formula (Ib')
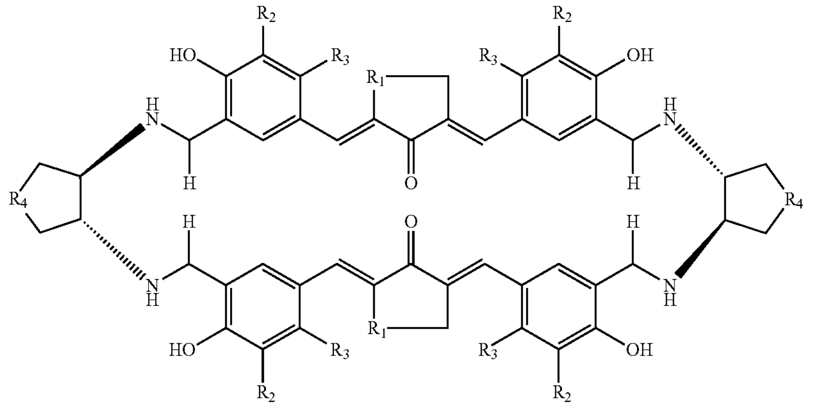
Wherein,
$R_1$=, $C_1$-$C_3$ alkyl, —$CH_2$NH—
$R_2$=—H, —$CF_3$, $C_1$-$C_4$ alkyl, Halogen, haloalkyl, alkoxy
$R_3$=—H, $C_1$-$C_{10}$ alkyl,
$R_4$=$C_1$-$C_3$ alkyl.
In another aspect the present invention provides (1S,2S) tetra-aza corand of formula (Ia")
Formula (Ia")
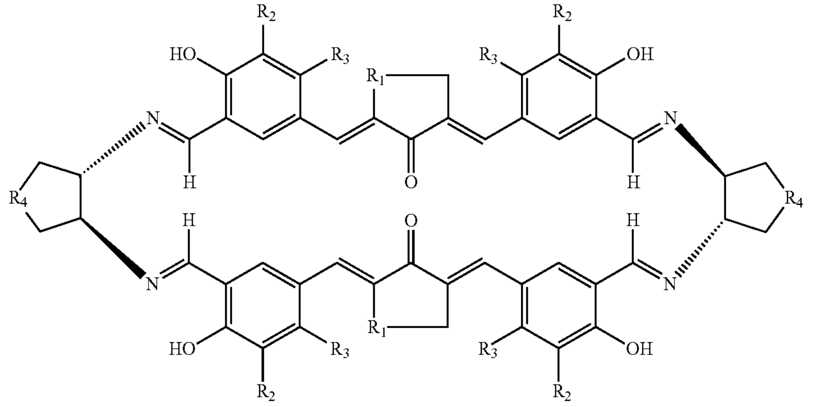

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

In another aspect the present invention provides (1R,2R) tetra-aza corand of formula (Ib")

Formula (Ib″)

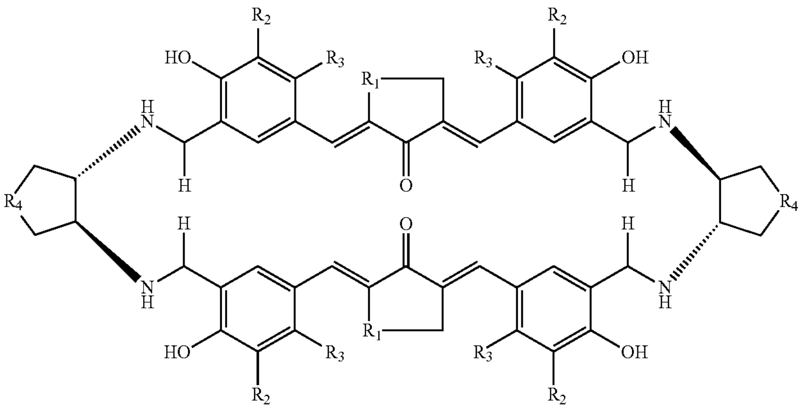

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

In another aspect the present invention provides (1R,2R) tetra-aza corand of formula From Racemic Diamino Cyclohexane

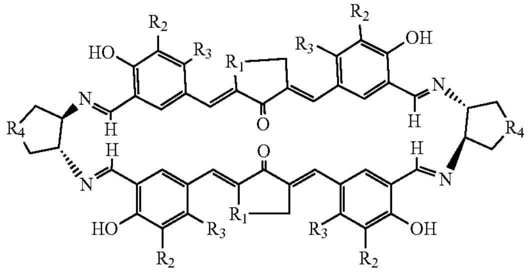

OR

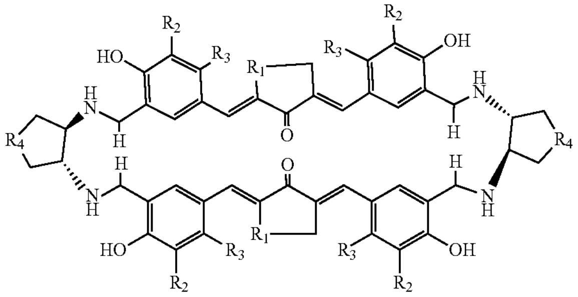

-continued

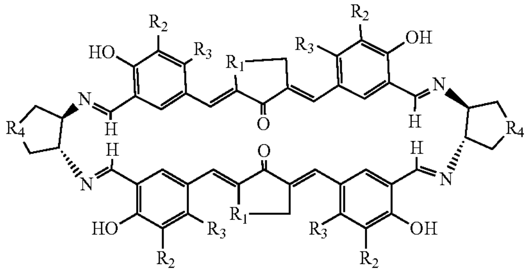

OR

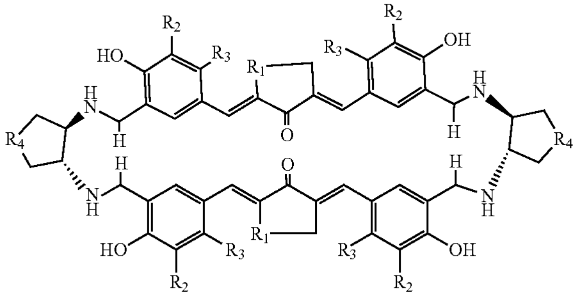

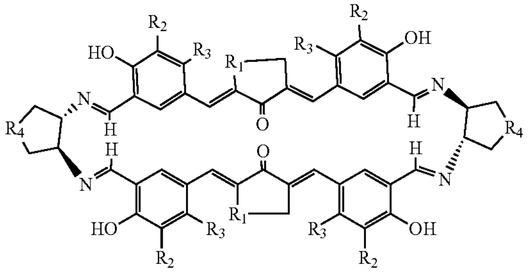

OR

-continued

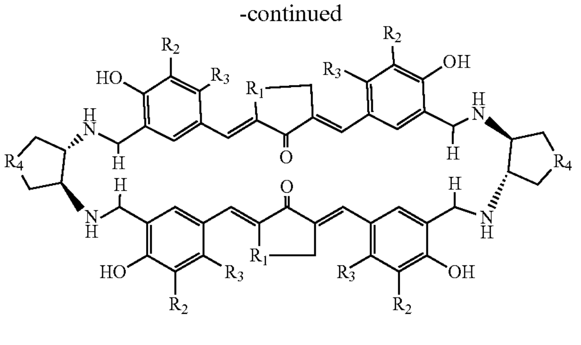

In another aspect the present invention relates to tetra-aza corand of formula (Ia) and formula (Ib) non-covalently bound to therapeutic/bioactive agents or drugs such as Flutamide, Nilutamide, Gemcitabin, Dasatinib, Methotrexate, Cis-platin as carriers for therapeutics delivery.

In another aspect, the present invention provides biocompatible corand attached to "therapeutic/bioactive" agents by non-covalent interaction; H bonding; ion-ion interaction or charge transfer interactions that are cleaved of biologically or photolytic under acidic/basic pH conditions and/or at high temperature to release the "therapeutic/bioactive agents".

BRIEF DESCRIPTION OF THE FIGURES

The accompanying drawings, which are incorporated in and constitute a part of this specification, illustrate several examples of the disclosed subject matter and together with the description, serve to explain certain principles of the disclosed subject matter.

FIG. 4*a*, 4*b*, 4*c*, 4*d* are expansions of FIG. 4

DETAILED DESCRIPTION OF THE INVENTION

Figure 1:
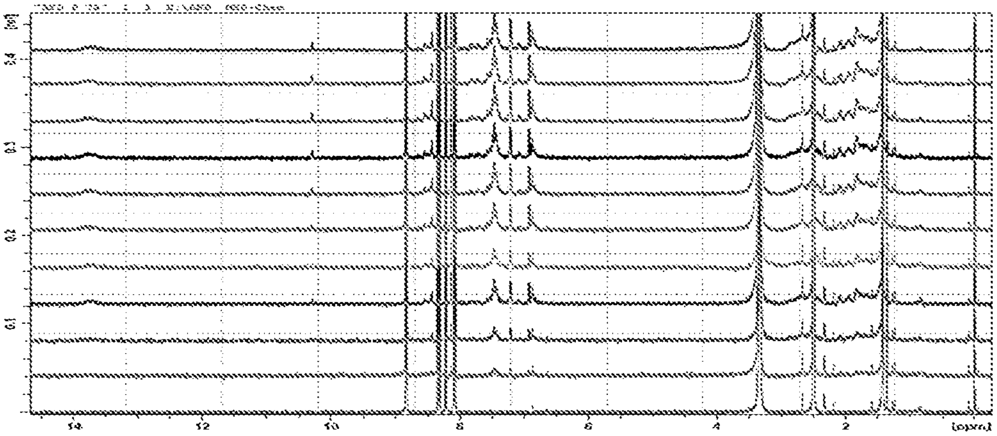
FIG. 1 NMR Titration to understand the interaction between the tetra iminocorand-3 and the drug Niluamide.
Figure 1A:
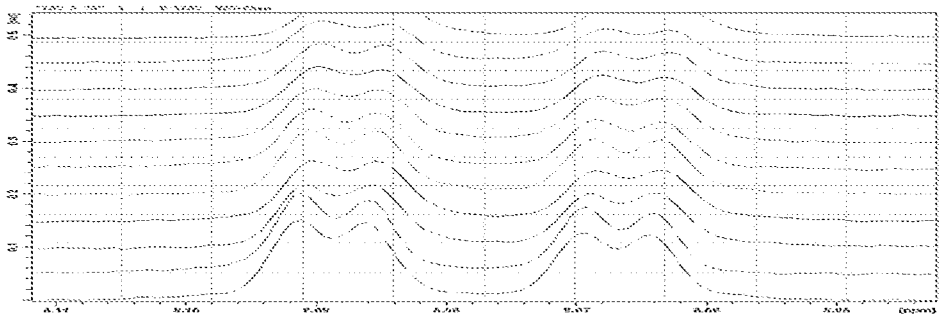
FIG. 1*a*, 1*b* are expansions of FIG. 1
Figure 1B:
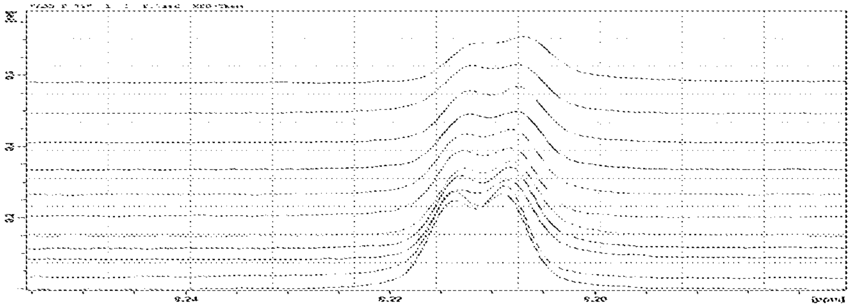

The compounds, compositions, articles, devices, and methods described herein can be understood more readily by reference to the following detailed description of specific aspects of the disclosed subject matter and the Examples and Figures.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

The term "corands" refers to monocyclic compounds which contain electron donor atoms or acceptor atoms, which are electron rich or deficient, and which are capable of complexing with particular cations or anions or neutral molecule because of their unique structures. Because of the unique sizes and geometries of particular corands, they are adaptable to complexing with various ions or molecules.

The term "therapeutic/bioactive agents" is drugs such as Flutamide, Nilutamide, Gemcitabin, Dasatinib, Methotrexate, Cis-platin are intended to be coupled/attached non-covalently to corand of formula (Ia) and formula (Ib) as carriers for therapeutics drug delivery complexes. The therapeutic/bioactive agents can also be a drug molecule, which is intended to include both non-peptides and peptides.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$) alkyl" is mean to include, but not be limited to, trifluoromethyl, 2,2,2-trifluoroethyl, 4-chlorobutyl, 3-bromopropyl, and the like.

Each of the above terms (e.g., "alkyl," and "haloalkyl") are meant to include both substituted and unsubstituted forms.

The present invention a tetra-aza corand of formula (Ia) and formula (Ib) i.e monocyclic macrocycle corands. The novel tetra-aza corand of formula (Ia) and formula (Ib) with cavity walls made up of bis-hydroxybenzylidene cyclic ketone and tetra imine/amine moieties. The novel tetra-aza corand of formula (Ia) and formula (Ib) has the properties somewhat similar to calixarene molecules. The novel tetra-aza corand of formula (Ia) and formula (Ib) encapsulate various drug molecules, further derivatisations by attachment of different functional groups to the proposed corands is done.

The tetra-aza corand of formula (Ia) and formula (Ib) are converted into their folate salts in order to develop a targeted drug delivery system. Cancer cells have folate receptors over expressed on their cell membrane where the folate salts of corands with the encapsulated drug are expected to be preferentially driven. The approach will deliver the drug to the tumor cells leaving the healthy cells unaffected.

The therapeutic/bioactive agents are attached to tetra-aza corand of formula (Ia) and formula (Ib) via non-covalent interaction. The therapeutic/bioactive agents may be attached to oligomer via an optional non-covalent interaction prior to the macromolecular complex step, or may be subsequently grafted onto the macromolecular complex via an optional non-covalent interaction, or may be attached to the macromolecular complex as an inclusion complex or host-guest interactions.

The present invention includes all salt forms of those molecules that contain ionisable functional groups, such as basic and acidic groups. The term "pharmaceutically acceptable salts" includes salts of the active compounds which are prepared with relatively nontoxic acids or bases, depending on the particular substituents found on the compounds described herein. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogen phosphoric, sulfuric, monohydrogensulfuric, hydriodic, or phosphorous acids and the like, as well as the salts derived from relatively nontoxic organic acids like acetic, propionic, isobutyric, folic, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., *Journal of Pharmaceutical Science,* 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents but otherwise the salts are equivalent to the parent form of the compound for the purposes of the present invention.

The present invention relates to tetra-aza corand of formula (Ia) and formula (Ib) made up of bis-hydroxybenzylidene cyclic ketone moiety having a substantially enclosed volume and a framework structure, the compounds are designed as therapeutic carriers for molecule therapeutics delivery and pharmaceutical compositions thereof Formula (Ia)

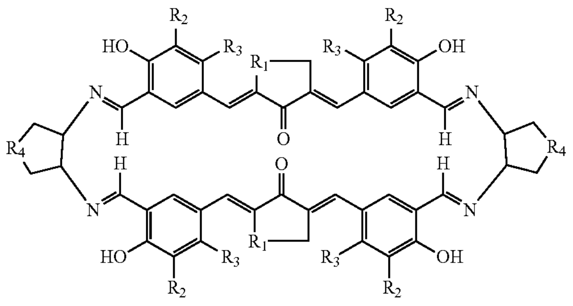

Formula (Ib)

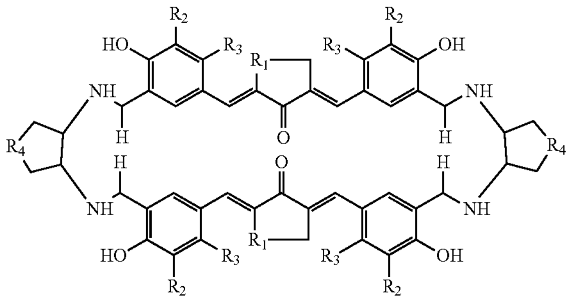

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

According to one embodiment of the present invention isomers of tetra-aza corand of formula (Ia) are (1R,2R) tetra-aza corand of formula (Ia') and (1S,2S) tetra-aza corand of formula (Ia") made up of bis-hydroxybenzylidene cyclic ketone moiety having a substantially enclosed volume and a framework structure, the compounds are designed as therapeutic carriers for molecule therapeutics delivery and pharmaceutical compositions thereof Formula (Ia′)

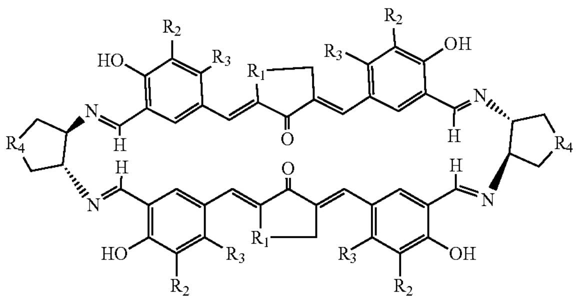

Formula (Ia″)

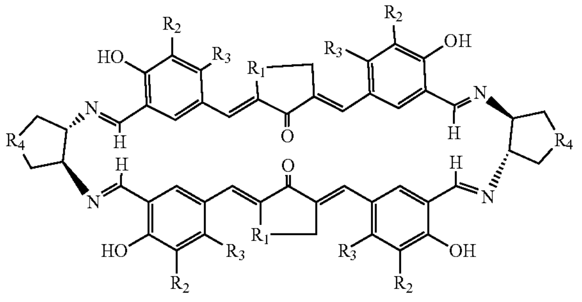

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

According to one embodiment of the present invention isomers of tetra-aza corand of formula (Ib) are (1R,2R) tetra-aza corand of formula (Ib') and (1S,2S) tetra-aza corand of formula (Ib") made up of bis-hydroxybenzylidene cyclic ketone moiety having a substantially enclosed volume and a framework structure, the compounds are designed as therapeutic carriers for molecule therapeutics delivery and pharmaceutical compositions thereof Formula (Ib′)

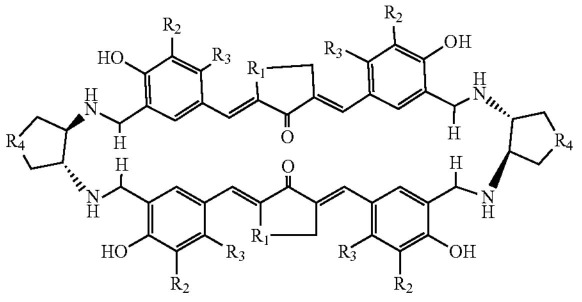

-continued

Formula (Ib″)

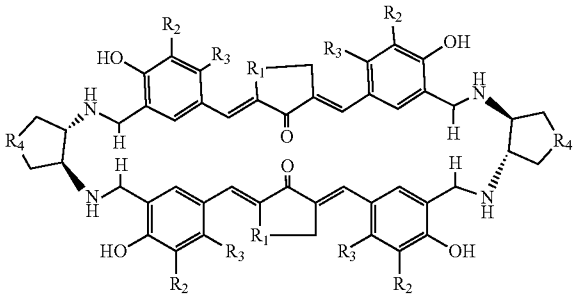

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

According to one embodiment of the present invention isomers of tetra-aza corand of formula (Ia) Racemic isomer comprises of

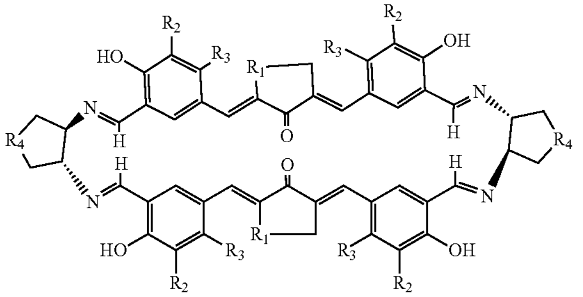

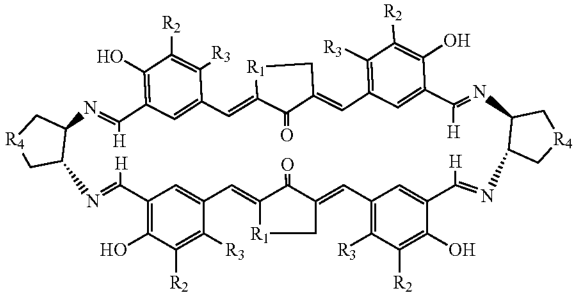

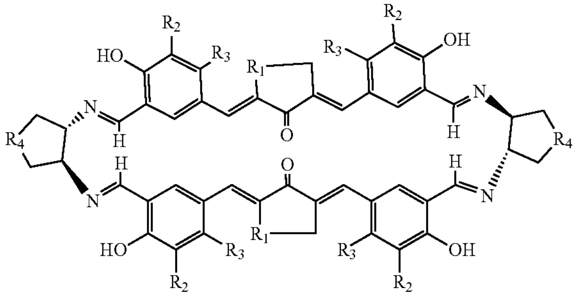

According to one embodiment of the present invention isomers of tetra-aza corand of formula (Ib) Racemic isomer comprises of

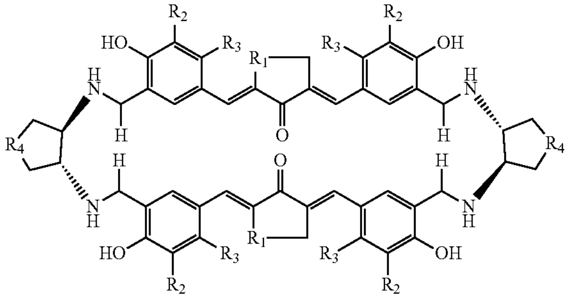

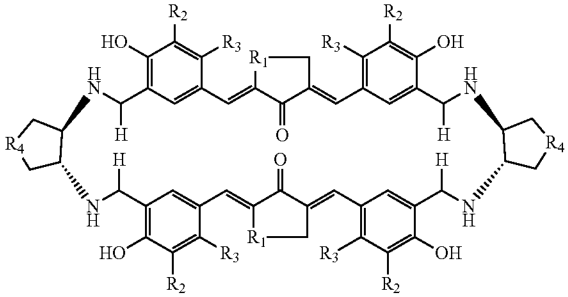

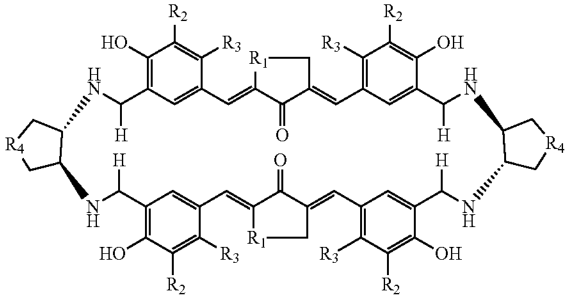

According to one embodiment of the present invention tetra-aza corand of formula (Ia) and formula (Ib) having a substantially enclosed volume and a framework structure, the compounds are designed as therapeutic carriers for molecule therapeutics delivery and pharmaceutical compounds such as Flutamide, Nilutamide, Gemcitabine, Methotrexate, Cis-platin, Bicalutamide, Topilutamide, Oxaliplatin, Carboplatin, Busulfan that were dissolved into various solvents like Dichloromethane, Ethanol, Methanol, Dimethyl formamide, Dimethyl sulphoxide, Ether, Toluene, Anisole, Trifluoroacetic acid, Benzene, Water.

According to one embodiment of the present invention the tetra-aza corand of formula (Ia) and formula (Ib) made up of bis-hydroxybenzylidene cyclic ketone moiety wherein therapeutic molecule is attached to the macrocycle compound of formula (Ia) or Formula (Ib) by non-covalent interaction. The corand may also employ targeting agents. By selecting from a variety of linker groups and targeting ligands the corand present methods for controlled delivery of the therapeutic agents. On reaching a targeted site in the body of a patient, the therapeutic molecule can then be cleaved onto the site. The methods provide reduced toxicity and local delivery of therapeutics. The invention also relates to methods of treating subjects with the therapeutic compositions described herein. The invention further relates to methods for conducting a pharmaceutical business comprising manufacturing, licensing, or distributing kits containing or relating to the polymeric compounds described herein.

In one embodiment, the reactive functional group is a member selected from amines, such as a primary or secondary amine, hydrazines, hydrazides, and sulfonyl hydrazides. Amines can, for example, be acylated, alkylated or oxidized. Useful non-limiting examples of amino-reactive groups include N-hydroxysuccinimide (NHS) esters, sulfo-NHS esters, imidoesters, isocyanates, isothiocyanates, acyl halides, arylazides, p-nitrophenyl esters, aldehydes, sulfonyl chlorides and carboxyl groups.

According to one embodiment of the present invention the corand of Formula (Ia) and Formula (Ib) wherein therapeutic molecule is attached to the corand of Formula (Ia) or Formula (Ib) by non-covalent interaction; H bonding; ion-ion interaction or charge transfer between corand and therapeutic molecule.

According to one embodiment of the present invention the tetra-aza corand of formula (Ia) and formula (Ib) are prepared by bis-hydroxybenzylidene cyclic ketone moiety of formula (I). The compound of formula (I) is reacted a cycloalkane-1,2-diamine to obtain tetra-aza corand of formula (Ia) and formula (Ib).

Formula (I)

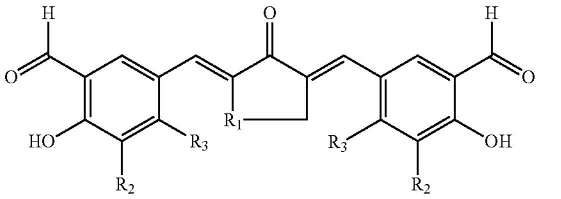

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, According to one embodiment of the present invention process for preparation of corand of formula (Ia)

Formula (Ia)

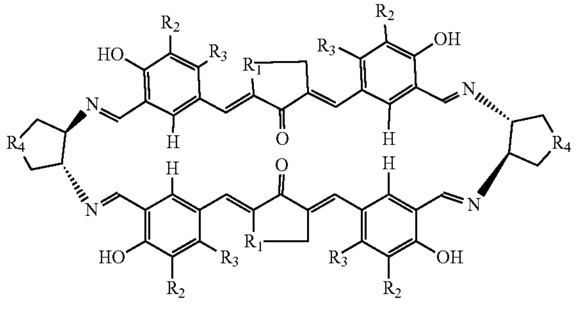

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

Example 1: Process for Synthesis of Corand (Ia)

2 L DCM was placed in a 5 L 3-necked round bottom flask equipped with 2 dropping funnels. One dropping funnel contained (0.003327 moles) of (1R,2R)-cycloalkane-1,2-diamine dissolved in 750 ml of DCM and another dropping funnel contained (0.0028 moles) of 5,5'-((1E,1'E)-(2-oxocyclicketone-1,3-diylidene)bis(methanylylidene))bis(2-hydroxybenzaldehyde) or its derivatives dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product. The crystallined product was filtered and dried in vacuum oven to obtain free flowing product.

Example 2: Process for Synthesis of Tetra Iminocorand-1

2 L DCM was placed in a 5 L 3-necked round bottom flask equipped with 2 dropping funnels. One dropping funnel contained (0.331 g, 0.00331 moles) of (1R,2R)-cyclopentane-1,2-diamine dissolved in 750 ml of DCM and another dropping funnel contained (1 g, 0.00276 moles) of 5,5'-((1E,1'E)-(2-oxocyclohexane-1,3-diylidene)bis(methanylylidene))bis(2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product in 68% yield.

Example 3: Process for Synthesis of Tetra Iminocorand-1'

2 L DCM was placed in a 5 L 3-necked round bottom flask equipped with 2 dropping funnels. One dropping funnel contained (0.378 g, 0.0033 moles) of (1S,2S)-cyclohexane-1,2-diamine dissolved in 750 ml of DCM and another dropping funnel contained (1 g, 0.0027 moles) of 5,5'-((1E,1'E)-(2-oxocyclohexane-1,3-diylidene)bis(methanylylidene))bis(2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product in 60% yield.

Example 4: Process for Synthesis of Tetra Iminocorand-1"

2 L DCM was placed in a 5 L 3-necked round bottom flask equipped with 2 dropping funnels. One dropping funnel contained (0.378 g, 0.0033 moles) of Trans-cyclohexane-1, 2-diamine dissolved in 750 ml of DCM and another dropping funnel contained (1 g, 0.0027 moles) of 5,5'-((1E,1'E)-(2-oxocyclohexane-1,3-diylidene)bis(methanylylidene))bis (2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange product as mixture of three isomers in 52% yield.

Example 5: Process for Synthesis of Tetra Iminocorand-2

2 L DCM was placed in a 5 L 3-necked round bottom flask equipped with 2 dropping funnels. One dropping funnel contained (0.23 g, 0.0023 moles) of (1R,2R)-cyclopentane-1,2-diamine dissolved in 750 ml of DCM and another dropping funnel contained (1 g, 0.0019 moles) of 5,5'-((1E,1'E)-(2-oxocyclohexane-1,3-diylidene)bis(methanylylidene))bis(3-bromo-2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product in 52% yield.

Example 6: Process for Synthesis of Tetra Iminocorand-3

2 L DCM was placed in a 5 L 3-necked round bottom flask equipped with 2 dropping funnels. One dropping funnel contained (0.378 g, 0.0033 moles) of (1R,2R)-cyclohexane-1,2-diamine dissolved in 750 ml of DCM and another dropping funnel contained (1 g, 0.0027 moles) of 5,5'-((1E,1'E)-(2-oxocyclohexane-1,3-diylidene)bis(methanylylidene))bis(2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product in 75% yield.

Example 7: Process for Synthesis of Tetra Iminocorand-4

2 L DCM was placed in a 5 L 3-necked round bottom flask equipped with 2 dropping funnels. One dropping funnel contained (0.26 g, 0.0023 moles) of (1R,2R)-cyclohexane-1,2-diamine dissolved in 750 ml of DCM and another dropping funnel contained (1 g, 0.0019 moles) of 5,5'-((1E,1'E)-(2-oxocyclohexane-1,3-diylidene)bis(methanylylidene))bis(3-bromo-2-hydroxybenzaldehyde) dissolved in 750 ml of DCM. Both solutions were added drop wise to mechanically stirred 2 L DCM over 7 to 8 hours. The reaction mixture was concentrated to 100 ml and kept for 12 to 15 hours at room temperature to obtain orange crystalline product in 40% yield.

Example 8: Drug Encapsulation Study with the Above Synthesized Tetraiminocorand NMR Titration -NMR titrations were recorded on 400 MHz Bruker instrument to study the encapsulation of drug in the corand. 0.6 ml $1\times10^{-2}$M solution of standard drugs (Flutamide, Nilutamideetc) were prepared in $CDCl_3$ and placed in the NMR tubes. NMR titrations were carried out by adding 30 μl, $2\times10^{-2}$M solution of tetraiminocorand.

FIG. 1 NMR Titration to understand the interaction between the tetra iminocorand-3 and the drug Niluamide. The NMR titration experiment revealed complete encapsulation of drug Niluamide in the tetra iminocorand-3. In case of Niluamide the double doublet of aromatic proton at 8.078 δ was shifted upfield at 8.075 δ. The doublet of aromatic proton at 8.211 δ and 8.325 δ was shifted upfield at 8.206 δ and 8.322 δ.

Example 9: Process for Synthesis of Corand (Ib)

The tetra iminocorand-(Ia) (0.001135 moles) was dissolved in 20 ml DCM (Dichloromethane) and 50 ml methanol. Added sodiumtriacetoxyborohydride (0.0090 moles) to magnetically stirred solution of tetra imino corand. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand was dried under high vacuum to obtain red free flowing solid.

Example 8: Process for Synthesis of Tetra Amino Corand-5

The tetra iminocorand-1 (1 g, 0.00117 moles) was dissolved in 10 ml DCM (Dichloromethane) and 50 ml methanol. Added sodiumtriacetoxyborohydride (1.98 g, 0.0094 moles) to magnetically stirred solution of tetra iminocorand-1. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand-5 was dried under high vacuum to obtain red free flowing solid in 80% yield.

Example 9: Process for Synthesis of Tetra Amino Corand-5'

The tetra iminocorand-1' (1 g, 0.001135 moles) was dissolved in 10 ml DCM (Dichloromethane) and 50 ml methanol. Added sodiumtriacetoxyborohydride (1.98 g, 0.0094 moles) to magnetically stirred solution of tetra iminocorand-5. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand-5' was dried under high vacuum to obtain red free flowing solid in 64% yield.

Example 10: Process for Synthesis of Tetra Amino Corand-5"

The mixture of isomers of tetra iminocorand-1" (1 g, 0.001135 moles) was dissolved in 10 ml DCM (Dichloromethane) and 50 ml methanol. Added sodiumtriacetoxyborohydride (1.925 g, 0.00908 moles) to magnetically stirred solution of tetra iminocorand-6. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed mixture of isomers of tetra amino corand-5" was dried under high vacuum to obtain red free flowing solid in 50% yield.

Example 11: Process for Synthesis of Tetraaminocorand-6

The tetra iminocorand-2 (1 g, 0.000855 moles) was dissolved in 10 ml DCM (Dichloromethane) and 50 ml methanol. Added sodiumtriacetoxyborohydride (1.45 g, 0.0068 moles) to magnetically stirred solution of tetraiminocorand-2. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand-6 was dried under high vacuum to obtain red free flowing solid in 85% yield.

Example 12: Process for Synthesis of Tetra Amino Corand-7

The tetra iminocorand-3 (1 g, 0.001135 moles) was dissolved in 10 ml DCM (Dichloromethane) and 50 ml methanol. Added sodiumtriacetoxyborohydride (1.925 g, 0.00908 moles) to magnetically stirred solution of tetraiminocorand-3. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand-7 was dried under high vacuum to obtain red free flowing solid in 76% yield.

Example 13: Process for Synthesis of Tetra Amino Corand-8

The tetra iminocorand-4 (1 g, 0.000835 moles) was dissolved in 10 ml DCM (Dichloromethane) and 50 ml methanol. Added sodiumtriacetoxyborohydride (1.416 g, 0.00668 moles) to magnetically stirred solution of tetraiminocorand-4. The solution was stirred for 30 minutes. Methanol was evaporated under vacuum completely. Residue was quenched in liquor ammonia and extracted with DCM. The DCM layer was dried over sodium sulphate and evaporated to obtain the desired product. The formed tetra amino corand-8 was dried under high vacuum to obtain red free flowing solid in 73% yield.

Example 14: Drug Encapsulation Study with the Above Synthesized Tetra Amino Corand NMR titration: -NMR titrations were recorded on 400 MHz Bruker instrument to study the encapsulation of drug in the corand. 0.6 ml $1\times10^{-2}$M solution of standard drugs (Flutamide, Nilutamide, Gemcitabin, Dasatinibetc) were prepared in DMSO-$d_6$ and placed in the NMR tubes. NMR titrations were carried out by adding 30 µl, $2\times10^{-2}$M solution of tetra aminocorand.

Figure 2:
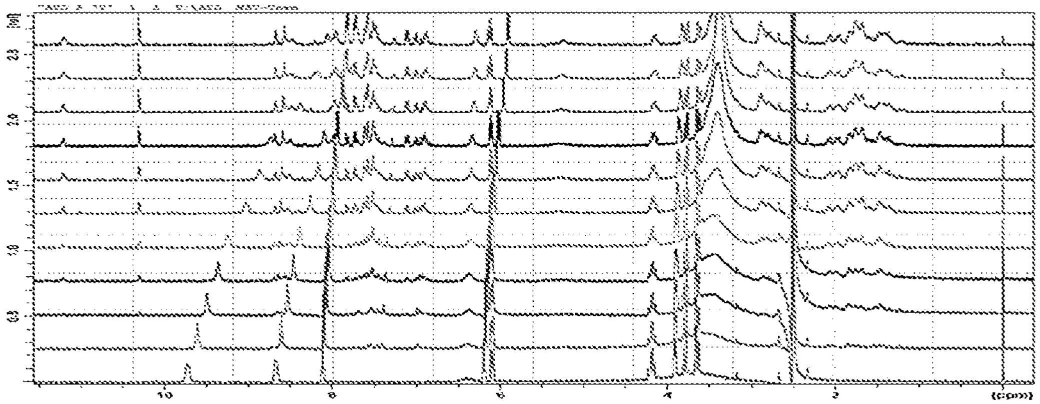
FIG. 2 NMR Titration to understand the interaction between the tetra amino corand-7 and the drug Gemcitabin.
Figure 2A:
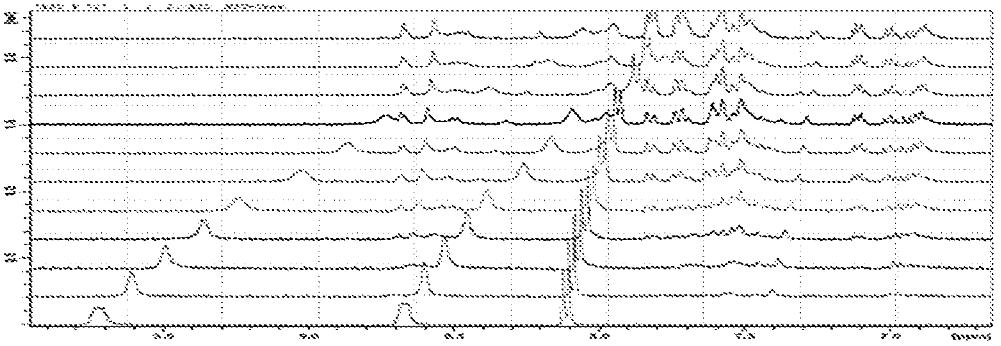
FIG. 2*a*, 2*b* are expansions of FIG. 2
Figure 2B:
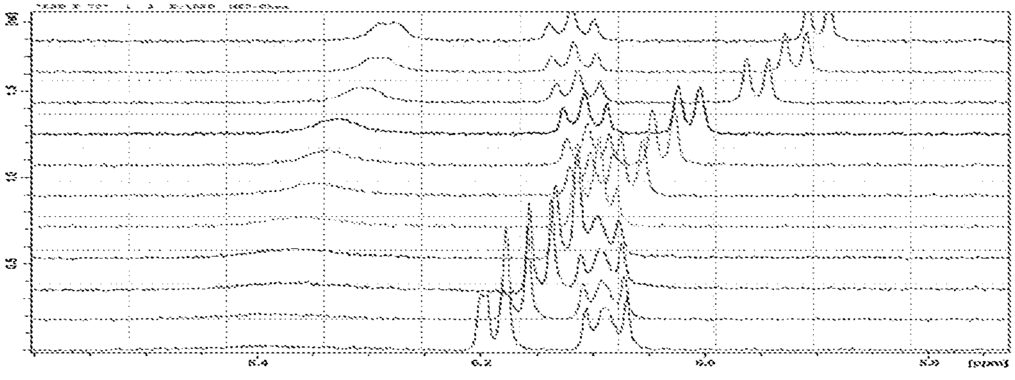

FIG. 2, NMR Titration to understand the interaction between the tetra amino corand-7 and the drug Gemcitabin. The NMR titration experiment revealed complete encapsulation of drug in the tetra amino corand-7. In case of Gemcitabin the signal of aliphatic OH group at 9.728 δ and 8.672 δ were shifted upfield to 8.15 δ and 7.952 δ respectively. The doublet of aromatic proton at 8.113 and 6.19 was shifted to upfield 7.828 δ and 5.898 δ respectively. The triplet of aliphatic proton at 6.088 δ was shifted downfield to 6.119 δ

Figure 3:
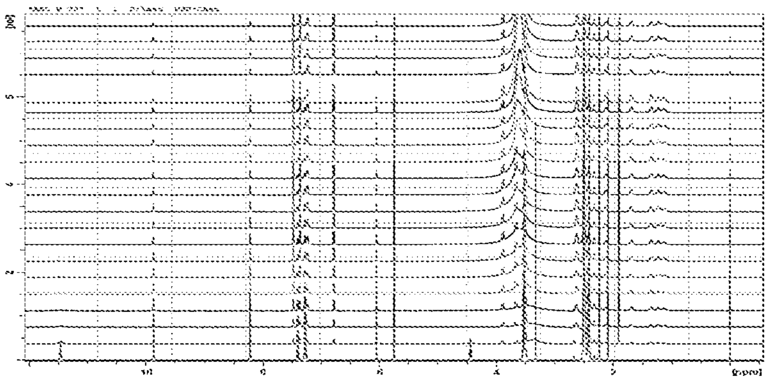
FIG. 3 NMR Titration to understand the interaction between the tetra amino corand-7 and the drug Dasatinib.
Figure 3A:
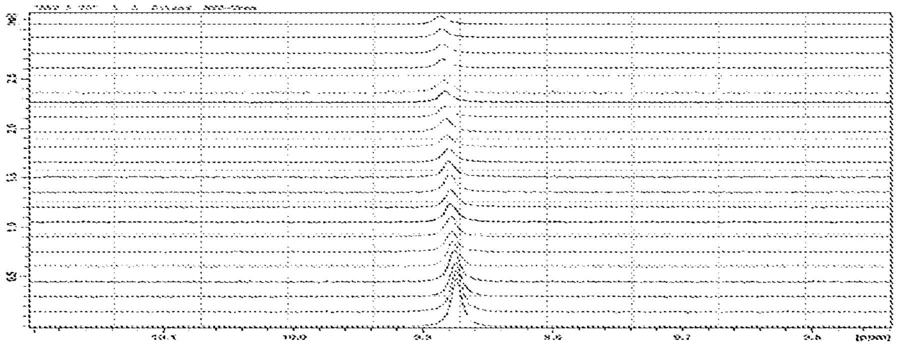
FIG. 3*a*, 3*b* are expansions of FIG. 1
Figure 3B:
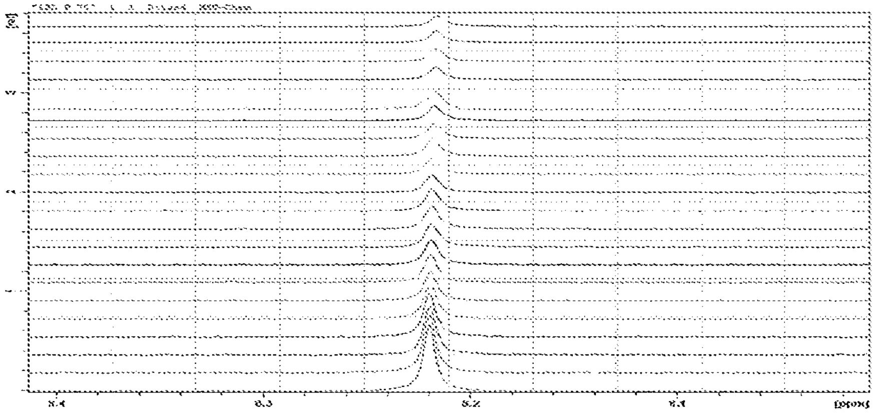

FIG. 3, NMR Titration to understand the interaction between the tetra amino corand-7 and the drug Dasatinib. The NMR titration experiment revealed complete encapsulation of drug in the tetra amino corand-7. In case of Dasatinib the singlet of aromatic proton at 8.220 δ was shifted upfield to 8.218 δ. The singlet of secondary amine at 9.867 δ was shifted to downfield at 9.887 δ.

Figure 4:
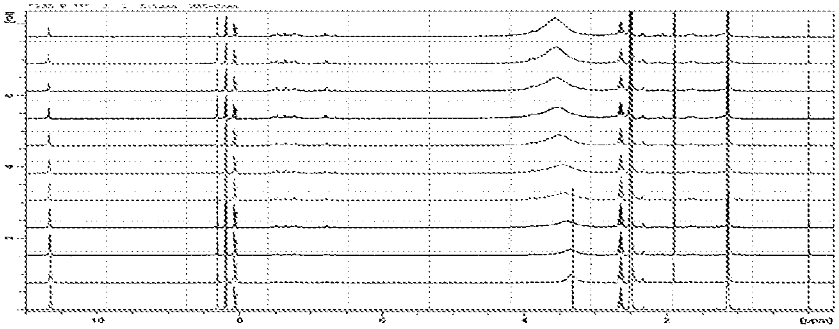
FIG. 4 NMR Titration to understand the interaction between the tetra amino corand-7 and the drug Flutamide.
Figure 4B:
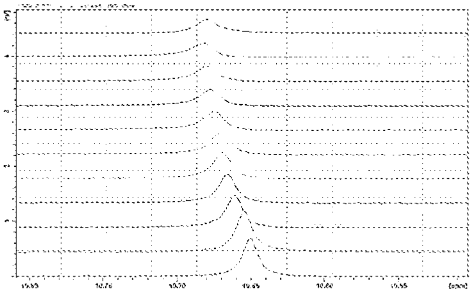
Figure 4C:
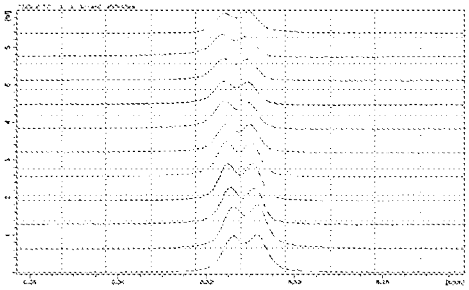
Figure 4D:
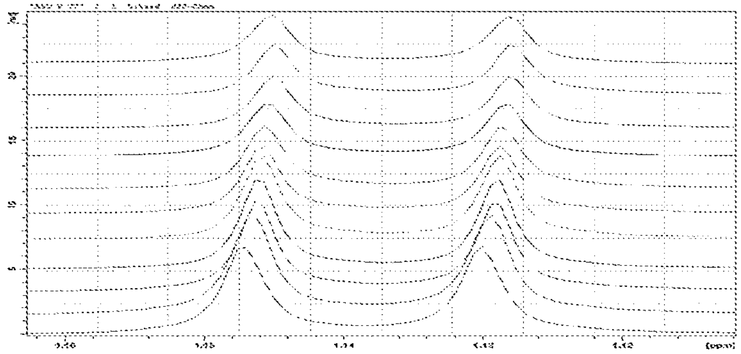
Figure 5:
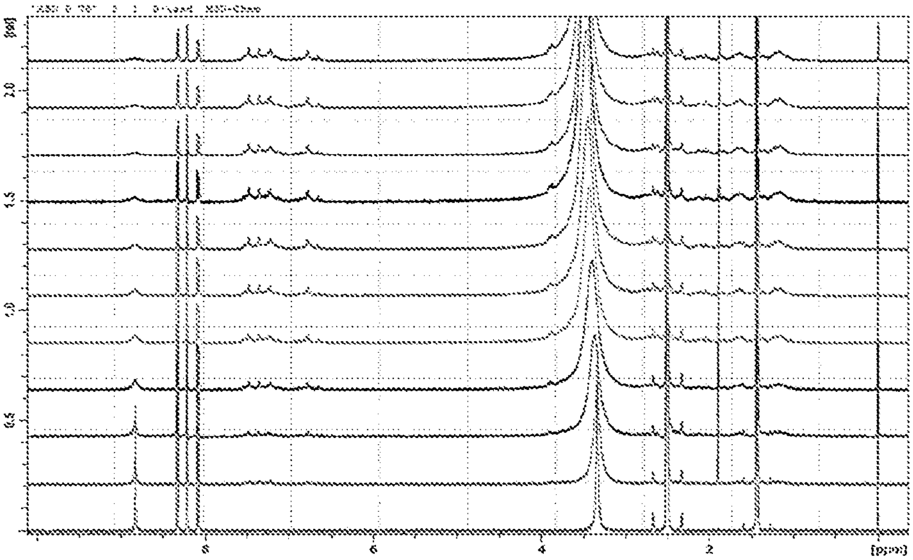
FIG. 5 NMR Titration to understand the interaction between the tetra amino corand-7 and the drug Nilutamide.
Figure 5A:
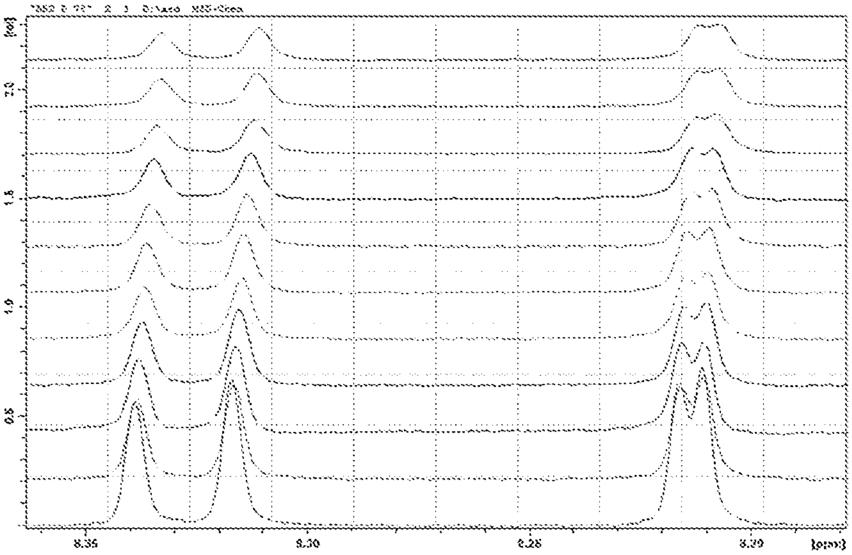
FIG. 5*a* are expansions of FIG. 5

FIG. 4, NMR Titration to understand the interaction between the tetra amino corand-7 and the drug Flutamide. The NMR titration experiment revealed complete encapsulation of drug in the tetra amino corand-7. In case of Flutamide the signal of aromatic doublet at 8.311 δ and 8.199 δ were shifted to 8.313 δ and 8.196 δ respectively. The singlet of secondary amide group at 10.650 δ was shifted downfield to 10.680 δ. The doublet of methyl proton at 1.138 δ was shifted upfield to 1.136 δ. FIG. 5, NMR Titration to understand the interaction between the tetra amino corand-7 and the drug Nilutamide. The NMR titration experiment revealed complete encapsulation of drug in the tetra amino corand-7. In case of Nilutamide the double doublet of aromatic proton at 8.328 δ and doublet at 8.2135 δ was shifted upfield to 8.322 δ and 8.209 δ.

According to One Embodiment of the Present Invention Process for Preparation of Salts of Corand of Formula (Ic):

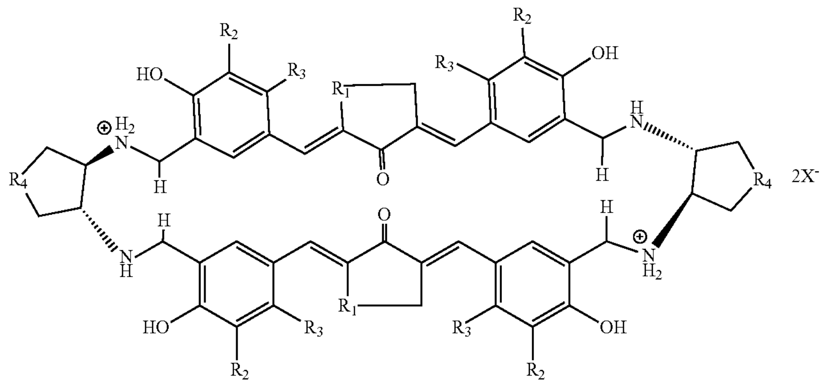

Wherein, $R_1$=, $C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=$C_1$-$C_3$ alkyl.

$X^-$=Folate, chloride, acetate

Example 15: General Process for Formation of Folate Salt

The solution of folic acid (0.001125 moles) dissolved in N, N-Dimethylformamid (5 ml) was added dropwise to the solution of tetraaminocorand dissolved in N, N-Dimethylformamide (5 ml). The folate salt gets precipitated instantly. The precipitates were filtered, washed with the N, N-Dimethylformamide, methanol, dichloromethane and dried under vacuum. The free flowing salt was obtained.

Example 16: Process for Formation of Folate Salt of Tetraaminocorand-5

The solution of folic acid (0.001162 moles, 0.512 g) dissolved in N, N-Dimethylformamid (5 ml) was added dropwise to the solution of tetraaminocorand-5 (0.500 g) dissolved in N, N-Dimethylformamide (5 ml). The folate salt gets precipitated instantly. The precipitates were filtered, washed with the N, N-Dimethylformamide, methanol, dichloromethane and dried under vacuum. The free flowing salt was obtained with 68% yield.

Example 17: Process for Formation of Folate Salt of Tetraaminocorand-6

The solution of folic acid (0.00085 moles, 0.375 g) dissolved in N, N-Dimethylformamid (5 ml) was added dropwise to the solution of tetraaminocorand-6 (0.500 g) dissolved in N, N-Dimethylformamide (5 ml). The folate salt gets precipitated instantly. The precipitates were filtered, washed with the N, N-Dimethylformamide, methanol, dichloromethane and dried under vacuum. The free flowing salt was obtained with 67% yield.

Example 18: Process for Formation of Folate Salt of Tetra Aminocorand-7

The solution of folic acid (0.001125 moles, 0.49680 g) dissolved in N, N-Dimethylformamide (5 ml) was added dropwise to the solution of tetraaminocorand-7 (0.500 g) dissolved in N, N-Dimethylformamide (5 ml). The folate salt gets precipitated instantly. The precipitates were filtered, washed with the N, N-Dimethylformamide, methanol, dichloromethane and dried under vacuum. The free flowing salt was obtained with 70% yield.

Example 19: Process for Formation of Folate Salt of Tetraaminocorand-8

The solution of folic acid (0.00083 moles, 0.366 g) dissolved in N, N-Dimethylformamid (5 ml) was added dropwise to the solution of tetraaminocorand-8 (0.500 g) dissolved in N, N-Dimethylformamide (5 ml). The folate salt gets precipitated instantly. The precipitates were filtered, washed with the N, N-Dimethylformamide, methanol, dichloromethane and dried under vacuum. The free flowing salt was obtained with 66% yield.

Example 20: Process for Formation of Hydrochloride Salt

The solution of tetraaminocorand (0.00056 moles) was dissolved in methanol (25 ml). HCl gas was passed for around 10 minutes to precipitate out the hydrochloride salt. The salt was filtered, washed with the methanol followed by dichloromethane and dried under vacuum. The free flowing salt was obtained.

Example 21: Process for Formation of Hydrochloride Salt of Tetraaminocorand-5

The solution of tetraaminocorand-5 (0.00058 moles, 0.500 g) was dissolved in methanol (25 ml). HCl gas was passed for around 10 minutes to precipitate out the hydrochloride salt.

The salt was filtered, washed with the methanol followed by dichloromethane and dried under vacuum. The free flowing salt was obtained with 64% yield.

Example 22: Process for Formation of Hydrochloride Salt of Tetraaminocorand-6

The solution of tetraaminocorand-6 (0.000424 moles, 0.500 g) was dissolved in methanol (25 ml). HCl gas was passed for around 10 minutes to precipitate out the hydrochloride salt. The salt was filtered, washed with the methanol followed by dichloromethane and dried under vacuum. The free flowing salt was obtained with 63% yield.

Example 23: Process for Formation of Hydrochloride Salt of Tetraaminocorand-7

The solution of tetraaminocorand-7 (0.00056 moles, 0.500 g) was dissolved in methanol (25 ml). HCl gas was passed for around 10 minutes to precipitate out the hydrochloride salt. The salt was filtered, washed with the methanol followed by dichloromethane and dried under vacuum. The free flowing salt was obtained with 62% yield.

Example 24: Process for Formation of Hydrochloride Salt of Tetraaminocorand-8

The solution of tetraaminocorand-8 (0.000415 moles, 0.500 g) was dissolved in methanol (25 ml). HCl gas was passed for around 10 minutes to precipitate out the hydrochloride salt. The salt was filtered, washed with the methanol followed by dichloromethane and dried under vacuum. The free flowing salt was obtained with 60% yield.

Example 25: General Process for Formation of Acetate Salt

The solution of tetra-aminocorand (0.00056 moles) was dissolved in methanol (25 ml). Acetic acid was added drop wise. The reaction mixture was stirred for 4 h at 30-40° C. The products, which were obtained after removal of methanol, was washed with the methanol followed by dichloromethane and dried under vacuum. The free flowing salt was obtained.

Example 26: Process for Formation of Acetate Salt of Tetraaminocorand-5

The solution of tetraaminocorand-5 (0.00058 moles, 0.500 g) was dissolved in methanol (25 ml). Acetic acid (0.00116 moles) was added drop wise. The reaction mixture was stirred for 4 h at 30-40° C. The products, which were obtained after removal of methanol, was washed with the methanol followed by dichloromethane and dried under vacuum. The free flowing salt was obtained with 70% yield.

Example 27: Process for Formation of Acetate Salt of Tetraaminocorand-6

The solution of tetraaminocorand-6 (0.000424 moles, 0.500 g) was dissolved in methanol (25 ml). Acetic acid (0.000848 moles) was added drop wise. The reaction mixture was stirred for 4 h at 30-40° C. The products, which were obtained after removal of methanol, was washed with the methanol followed by dichloromethane and dried under vacuum. The free flowing salt was obtained with 73% yield.

Example 28: Process for Formation of Acetate Salt of Tetraaminocorand-7

The solution of tetraaminocorand-7 (0.00056 moles, 0.500 g) was dissolved in methanol (25 ml). Acetic acid (0.00112 moles) was added drop wise. The reaction mixture was stirred for 4 h at 30-40° C. The products, which were obtained after removal of methanol was washed with the methanol followed by dichloromethane and dried under vacuum. The free flowing salt was obtained with 80% yield.

Example 29: Process for Formation of Acetate Salt of Tetraaminocorand-8

The solution of tetraaminocorand-8 (0.000415 moles, 0.500 g) was dissolved in methanol (25 ml). Acetic acid (0.00083 moles) was added drop wise. The reaction mixture was stirred for 4 h at 30-40° C. The products, which were obtained after removal of methanol, was washed with the methanol followed by dichloromethane and dried under vacuum. The free flowing salt was obtained with 78% yield.

Example 30: Drug Encapsulation Study with the Above Synthesized Salts of Tetra Amino Corand NMR titration: -NMR titrations were recorded on 400 MHz Bruker instrument to study the encapsulation of drug in the folate salt of corand. 0.6 ml $1\times10^{-2}$M solution of standard drugs (Gemcitabin, Dasatinibetc) were prepared in DMSO-$d_6$ and placed in the NMR tubes. NMR titrations were carried out by adding 15 μl, $2\times10^{-2}$M solution of folate salt of tetraaminocorand.

Figure 6:
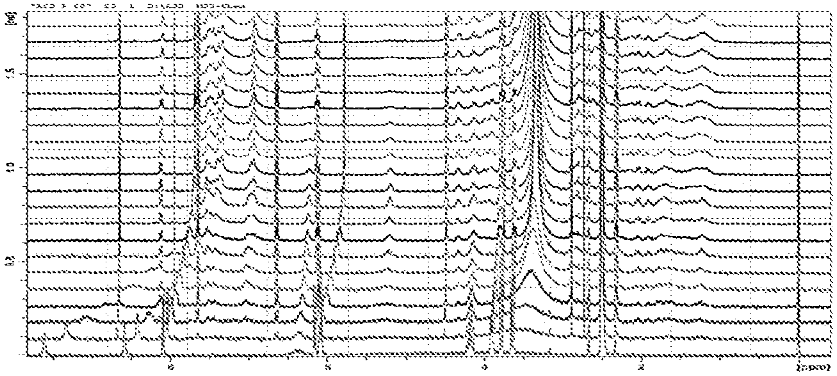
FIG. 6 NMR Titration to understand the interaction between the tetra amino folate corand and the drug Gemcitabin.
Figure 6A:
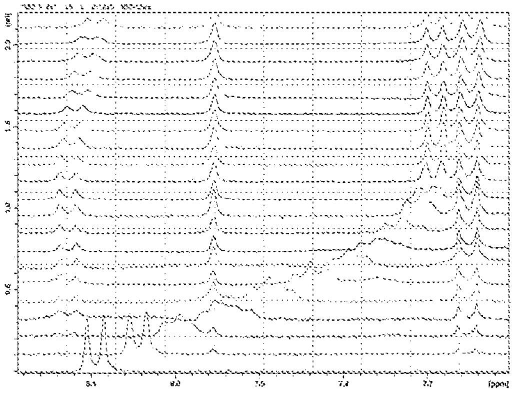
FIG. 6*a*, 6*b*, 6*c* are expansions of FIG. 6
Figure 6B:
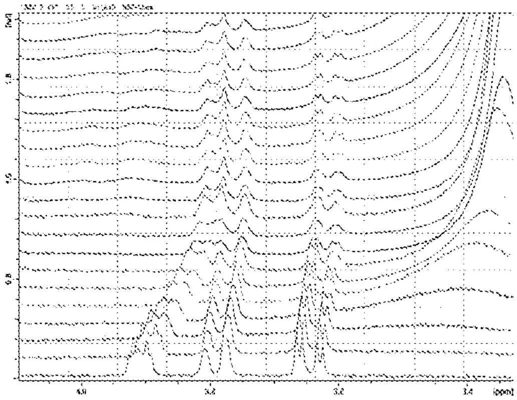
Figure 6C:
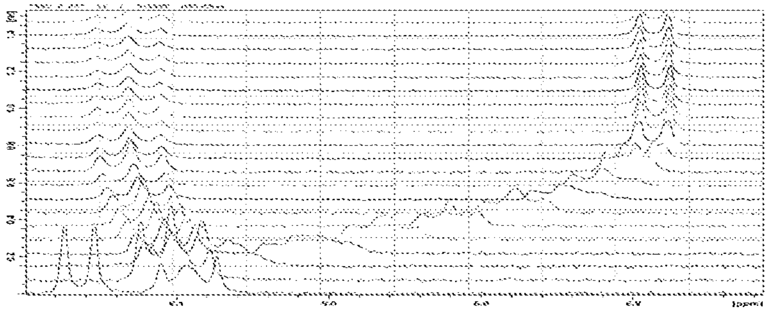

FIG. 6 NMR Titration to understand the interaction between the tetra amino folate corand and the drug Gemcitabin. The NMR titration experiment revealed complete encapsulation of drug in the tetra amino folate corand. In case of Gemcitabin the doublet of aromatic proton at 8.095 δ and 6.164 δ was shifted upfield to 7.691 δ and 5.786 δ. The triplet of aliphatic proton was shifted down field from 6.092 δ to 6.131 δ. In case of Gemcitabin titration aliphatic e proton at 3.661 δ and 3.629 δ were shifted upfield at 3.631 δ and 3.601 δ.

Figure 7:
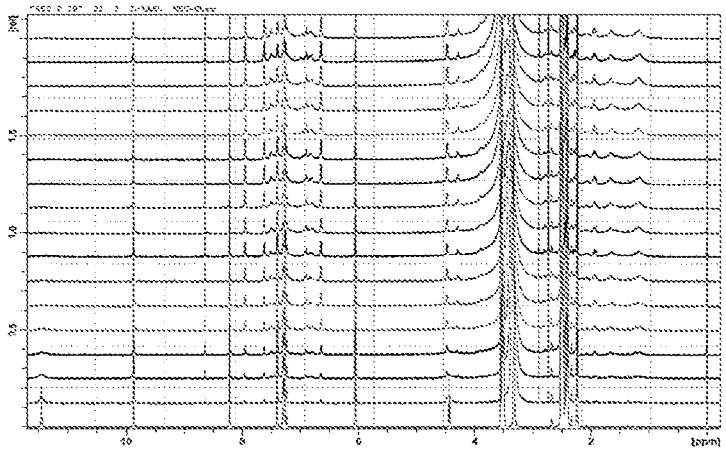
FIG. 7 NMR Titration to understand the interaction between the tetra amino folate corand and the drug Dasatinib.
Figure 7A:
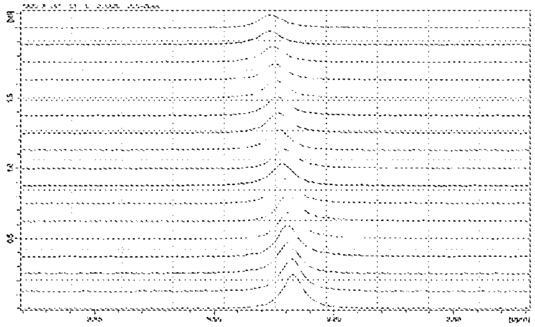
FIG. 7*a*, 7*b* are expansions of FIG. 7.
Figure 7B:
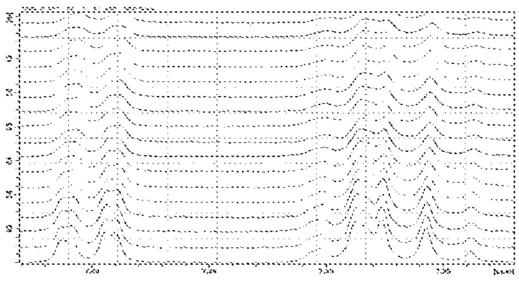

FIG. 7 NMR Titration to understand the interaction between the tetra amino folate corand and the drug Dasatinib. The NMR titration experiment revealed complete encapsulation of drug in the tetra amino folate corand. In case of Dasatinib the doublet of aromatic proton at 7.282 δ and double doublet at 7.402 δ were shifted upfield to 7.278 δ and 7.396 δ respectively The singlet of secondary amine at 9.867 δ was shifted downfield at 9.877 δ.

Example 31: Drug Encapsulation Study with the Above Synthesized Tetra Amino Corand-5'

NMR titration: -NMR titrations were recorded on 400 MHz Bruker instrument to study the encapsulation of drug in the folate salt of corand. 0.6 ml $1\times10^{-2}$M solution of standard drugs (Gemcitabin, Dasatinibetc) were prepared in DMSO-$d_6$ and placed in the NMR tubes. NMR titrations were carried out by adding 15 μl, $2\times10^{-2}$M solution of tetra amino corand-5'.

Figure 8:
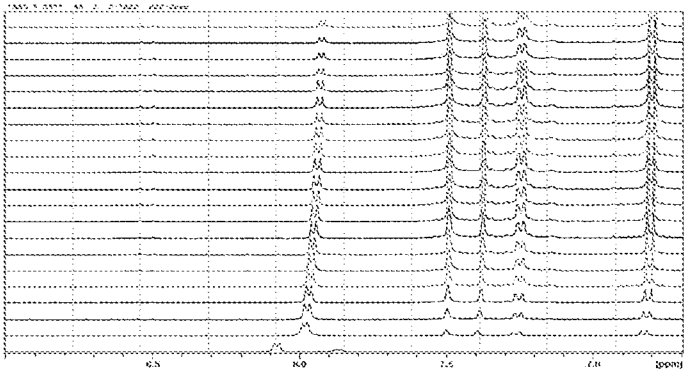
FIG. 8 NMR Titration to understand the interaction between the tetra amino corand-7 and the drug Capecitabine. a) Expansion of downfield region b) Expansion of Up-field region c) Complete NMR spectra FIG. 9 Cumulative release of capecitabine at pH 7.4 and pH 5.5 from inclusion complex of tetra amino corand-7 with methotrexate
Figure 8A:
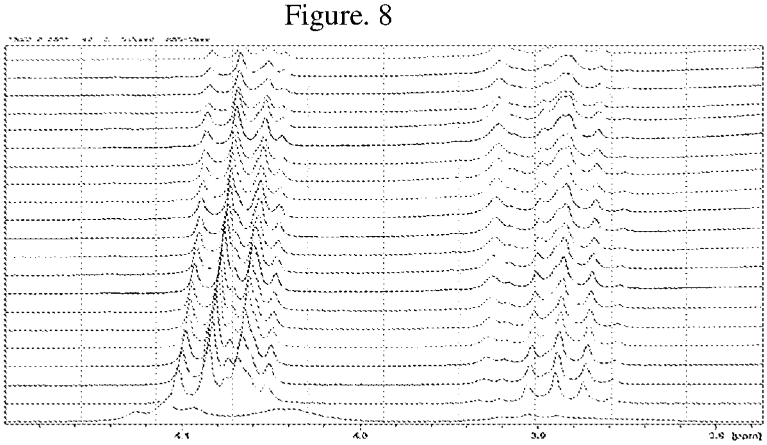
Figure 8B:
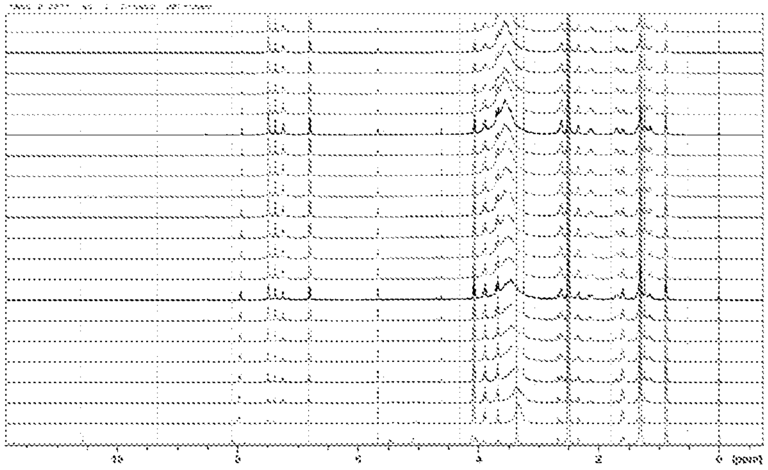

FIG. 8 NMR Titration to understand the interaction between the tetra amino corand-5' and the drug Capecitabine. a) Expansion of downfield region b) Expansion of Up-field region c) Complete NMR spectra The cumulative release of methotrexate inclusion complex with tetra amino corand-5' was studied in phosphate buffer at pH 7.4 and pH 5.5. The result reveals sustained release of methotrexate. The result also suggests that the release is more at pH 5.5 as compare to pH 7.7.

Figure 9:
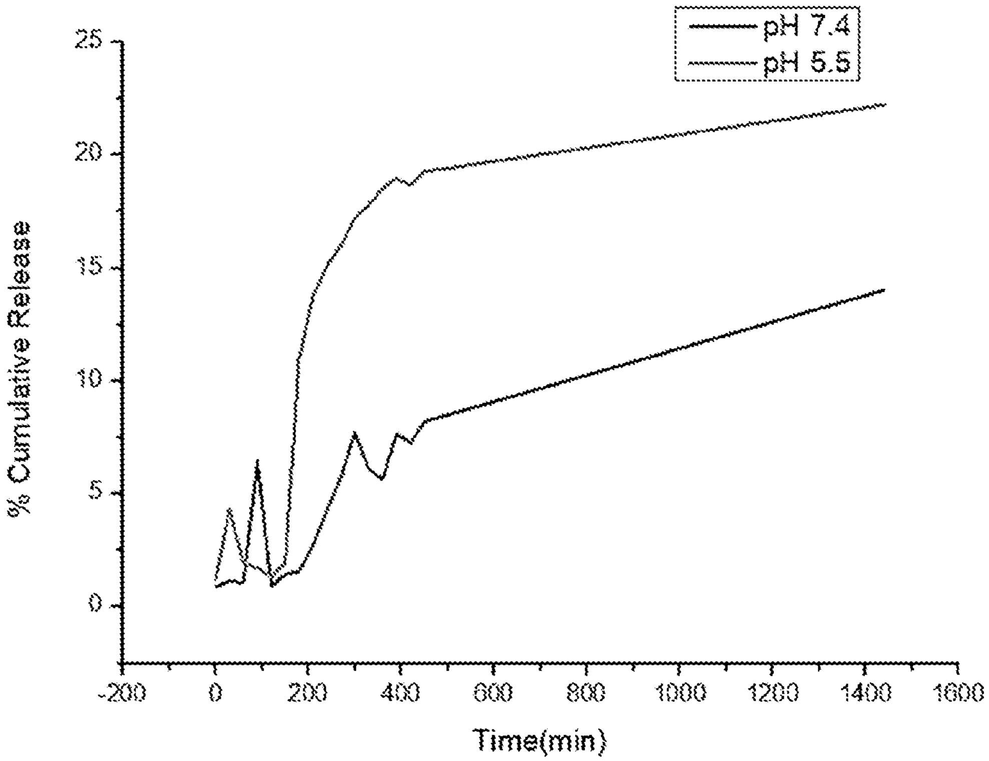

FIG. 9 Cumulative release of capecitabine at pH 7.4 and pH 5.5 from inclusion complex of tetra amino corand-5' with methotrexate Drug Binding Modes of Corands:

The corands will bind the drug molecules due to steric and interactional complementarity. The —OH (phenolic), —HC═N-(imino)/-NH-(Secondary amino) and —C═O (cyclic ketone) group will be responsible for making hydrogen bonding with the drug molecules. The benzylidene cyclic ketone group is also capable of establishing charge transfer interaction with the suitable drug molecule and making the stable host-guest complex.

We claim:

1. A tetra-aza corand compound of formula (Ia);

Formula (Ia)

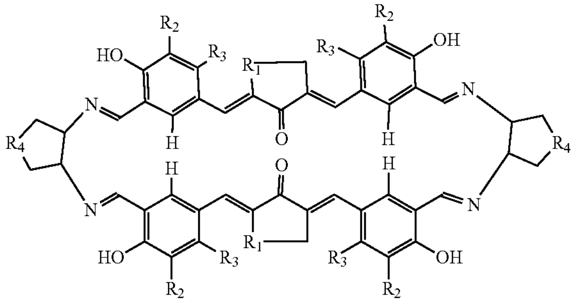

Wherein, $R_1$=—$C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=—$C_1$-$C_3$ alkyl.

2. The tetra-aza corand as claimed in claim 1 wherein, tetra-aza corand compound of formula (Ia) in isomeric form (1R,2R) tetra-aza corand of formula (Ia')

Formula (Ia')

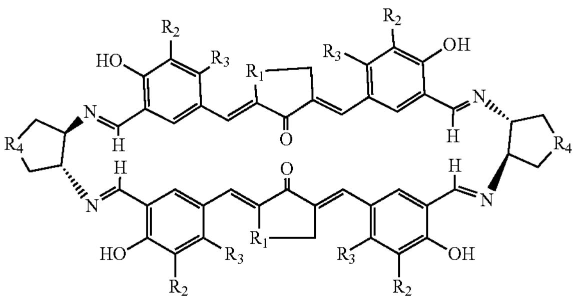

Wherein, $R_1$=—$C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=—$C_1$-$C_3$ alkyl.

3. The tetra-aza corand as claimed in claim 1 wherein, the isomeric form of tetra-aza corand compound of formula (Ia) is (1S,2S) tetra-aza corand of formula (Ia")

Formula (Ia")

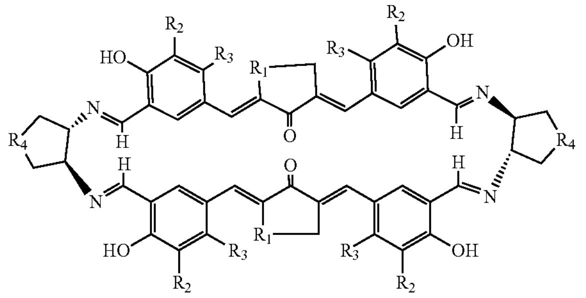

Wherein, $R_1$=—$C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=—$C_1$-$C_3$ alkyl.

4. A tetra-aza corand compound of formula (Ib);

Formula (Ib)

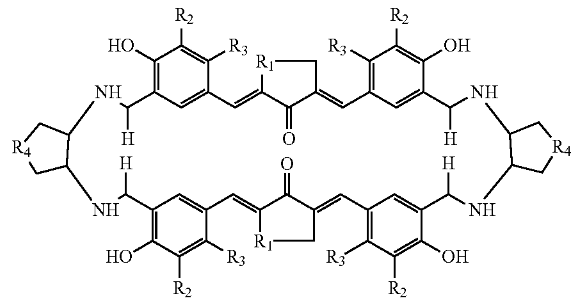

Wherein, $R_1$=—$C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=—$C_1$-$C_3$ alkyl.

5. The tetra-aza corand as claimed in claim 4 wherein, the isomeric form of tetra-aza corand compound of formula (Ib) is (1R,2R) tetra-aza corand of formula (Ib')

Formula (Ib')

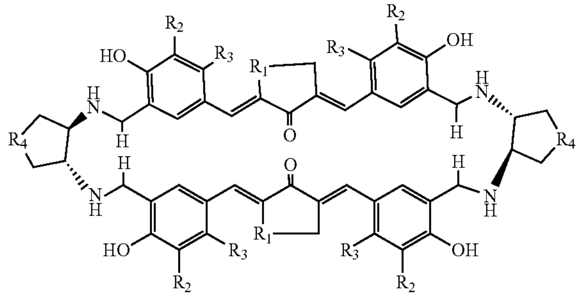

Wherein, $R_1$=—$C_1$-$C_3$ alkyl, —$CH_2NH$—

$R_2$=—H, —$CF_3$, $C_1$-$C_4$ alkyl, Halogen, haloalkyl, alkoxy $R_3$=—H, $C_1$-$C_{10}$ alkyl, $R_4$=—$C_1$-$C_3$ alkyl.

* * * * *